United States Patent
Nielsen

[11] Patent Number: 6,059,775
[45] Date of Patent: May 9, 2000

[54] MULTIFOCAL CORNEAL SCULPTURING

[76] Inventor: James M. Nielsen, 2339 Sunset Point Rd., Clearwater, Fla. 34625

[21] Appl. No.: 09/001,524

[22] Filed: Dec. 31, 1997

[51] Int. Cl.[7] ..................................................... A61N 5/06
[52] U.S. Cl. ..................................................... 606/5; 606/4
[58] Field of Search ............................... 606/4, 5, 6, 10, 606/11, 12, 17, 18

[56] References Cited

U.S. PATENT DOCUMENTS

| | | | |
|---|---|---|---|
| 4,636,211 | 1/1987 | Nielsen | 623/6 |
| 5,108,388 | 4/1992 | Trokel | 606/5 |
| 5,133,708 | 7/1992 | Smith | 606/5 |
| 5,152,759 | 10/1992 | Parel et al. | 606/5 |
| 5,158,572 | 10/1992 | Nielsen | 623/6 |
| 5,196,027 | 3/1993 | Thompson et al. | 623/5 |
| 5,277,911 | 1/1994 | Viegas et al. | 424/427 |
| 5,279,611 | 1/1994 | McDonnell et al. | 606/4 |
| 5,376,086 | 12/1994 | Khoobehi et al. | 606/4 |
| 5,423,801 | 6/1995 | Marshall et al. | 606/5 |
| 5,662,706 | 9/1997 | Legerton et al. | 623/6 |
| 5,748,282 | 5/1998 | Freeman | 351/161 |

OTHER PUBLICATIONS

"Wake Up and See the World," 1997 LCA Vision, Inc., LCA Vision Website page, 11 pages.

"Eye Operation Clears Path for NFL Runner," by Jarrett Bell, USA Today, Jun. 27, 1996.

*Primary Examiner*—Sonya Harris Ogugua
*Attorney, Agent, or Firm*—Lyon & Lyon LLP

[57] ABSTRACT

There is disclosed herein a method and system for corneal sculpting to create a multifocal refractive surface on the cornea of the eye. The refractive surface may comprise a central area and successive rings exposed outwardly toward the periphery and are of varying dioptric powers which may begin with the highest dioptric power in the center and decreasing powers of varying diopters progressing toward the periphery or vice-versa or alternating patterns of dioptric power, i.e., near/far, far/near or any combination. Furthermore, the multiple zones may be asymmetric, dicentric, ovoid, or the like. Suitable masks, barriers and iris diaphragms are described for facilitating sculpting of the different surfaces to achieve the desired multifocal refractive surfaces.

12 Claims, 2 Drawing Sheets

ND SCULPTURING

This invention relates to the eye and corneal surgery and, in particular to a system and method for corneal sculpturing for providing a multifocal refractive pattern to the cornea.

BACKGROUND

A significant percent of the human population develops an ocular refractive error requiring correction by glasses, contact lenses, or surgical procedures. Refractive errors result when the optical elements of the eye, the cornea and the lens, fail to image light directly on the retina. If the image is focused in front of the retina, myopia or nearsightedness exists; whereas, an eye which focuses images behind the retina is said to be hyperopic or farsighted. Furthermore, an eye which has power that varies significantly in different meridians is said to be astigmatic. The focusing power of the eye is measured in units called diopters, and the cornea is responsible for about two-thirds of the eye's sixty diopter refracting power with the lens contributing the remainder.

In addition to corrective lenses, that is glasses, contact lenses and inter-ocular lenses, opthalmologists have derived a number of surgical procedures which attempt to correct refractive errors. These involve various forms of profiling of the cornea. Example procedures of those as heretofore proposed are discussed in U.S. Pat. No. 5,423,801, No. 5,133,708, No. 5,196,027, and others, and the patents and articles cited therein. U.S. Pat. No. 5,423,801 describes a procedure for re-profiling the Bowman's membrane of the cornea of the eye, and in particular controlling laser radiation so that ablation terminates substantially within Bowman's membrane and not the underlying stroma. The re-profiling technique is for ablation and reshaping the cornea to change the profile or curvature thereof.

In addition to these surgical techniques, variable power optical lenses are widely used for correcting aberrations of the eye. One inter-ocular lens providing multifocal capabilities is described in U.S. Pat. No. 5,158,572. According to this patent, a multifocal lens can be formed having a substantially circular central region having a first optical power, surrounded by a plurality of concentric ring regions having at least two optical powers, one of which may be the first optical power.

SUMMARY OF THE INVENTION

According to the present invention, a multifocal refractive surface on the cornea of the human eye can be provided by corneal sculpturing, preferably of the stroma. The multifocal refractive surface comprises a plurality of refractive zones which may begin with the highest dioptric power in the center and decreasing powers of varying diopters progressing toward the periphery, or the reverse with the least amount of power in the center and a progressive increase in power as the periphery is reached, or any combination, i.e. near/far or far/near, and the like.

In order to obtain the desired refractive result in corneal refractive sculpturing, preferably a sculpturing barrier or shield is presented that will allow selected concentric or acentric zones to be sculpted one at a time or sculpted with multiple zones simultaneously. For example, in using an excimer laser for P.R.K. or Lasik procedures, the sculpting barrier is affixed to the cornea by direct apposition like a contact lens, or fixated by a suction device, so as to allow the laser energy to affect only the particular corneal zone selected for corneal refractive sculpting. A contact lens like barrier can be used that blocks laser energy from sculpting the protected areas. The protective barriers may have one or multiple apertures to allow the laser energy to sculpt the desired refractive power. The barriers or shields are constructed of materials impervious to the energy modality being used.

Accordingly, it is an object of the present invention to provide a multifocal refractive surface on the cornea of the human eye.

Another object of the present invention is to provide a multifocal refractive surface on or in the cornea of the human eye comprising a central area of one power, and one or more substantially concentric ring regions with at least two optical powers, one of which may be the first optical power.

Another object of the invention is to provide a corneal sculpturing method for forming a multifocal refractive surface in the stroma of the eye.

A further object of this invention is to provide a new form of corneal sculpting barrier.

BRIEF DESCRIPTION OF THE DRAWINGS

These and other objects and features of the present invention will become better understood through a consideration of the following description taken in conjunction with the drawings in which.

DETAILED DESCRIPTION

Figure 1:
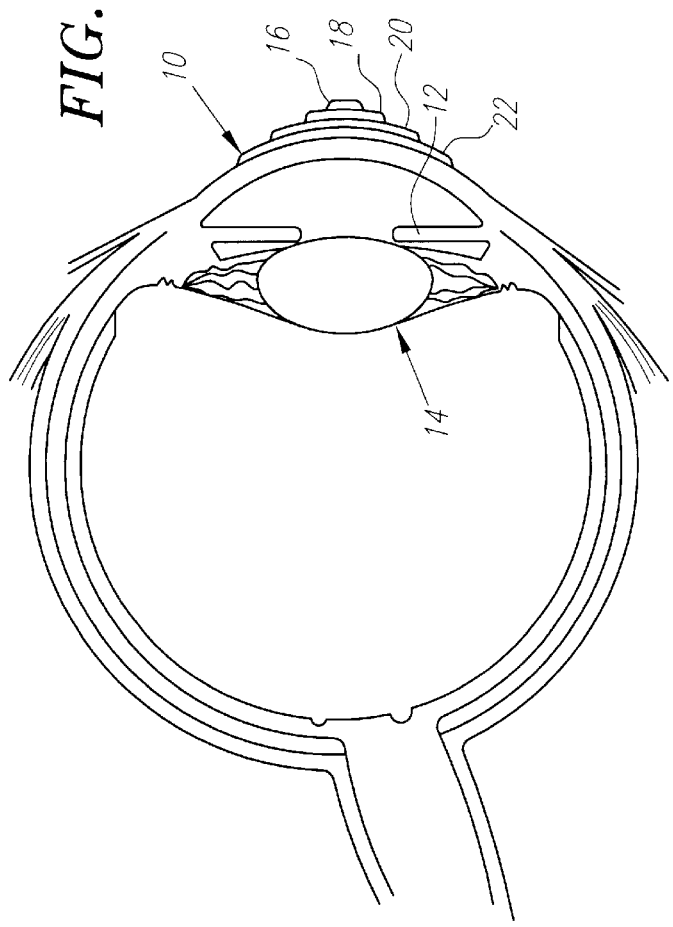
FIG. 1 is a vertical cross-sectional view of a human eye illustrating sculpted multiple zones.

Turning now to the drawings, and first to FIGS. 1 and 2, FIG. 1 illustrates a cross-sectional side view of the human eye, and shows the cornea 10, iris 12, and lens 14. The cornea 10 of the eye in FIG. 1 has been sculpted by a laser or other suitable source of energy to create a multifocal refractive surface comprising a central circular area 16, and a series of concentric refractive rings 18, 20, and 22. The manner in which the sculpting is accomplished will be discussed in further detail subsequently.

These refractive zones may begin, for example, with the highest dioptric power in the center 16 and with decreasing powers of varying diopters in zones 18, 20 and 22 or, alternatively, the reverse with the least amount of power in the center 16 and a progressive increase in power as the periphery of the cornea is reached and, further, may be any combination of alternating powers depending on the corrections desired. The energy source used, and which will be discussed later, reshapes the corneal surface and/or stroma to create the series of the concentrically spaced refractive rings 18, 20, 22, etc. and the center section 16, and the range can be of different diameters or widths, thicknesses and dioptric powers. These concepts can be useful for subjects whose accommodative process has decreased or is absent because of normal aging. The sculpting technology can enable these patients to focus for example at near (reading), intermediate, and distance (driving) without the need for glasses (bifocal, trifocal, progressive) or contact lenses.

Figure 2A:
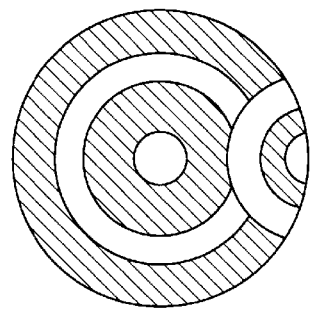
FIG. 2a illustrates in general form a multi-ring pattern for a barrier.

FIG. 2a illustrates a form of shield having a central circular area 30, and a plurality of concentric rings 31–34. This FIG. 2A illustrates in general the structure of a suitable shield, barrier or corneal mask, and which can be constructed so that one or more of the sections thereof functions as a sculpting barrier to thereby allow a selected zone or zones to be sculpted one at a time, or even sculpted with multiple zones simultaneously.

Figure 2C:
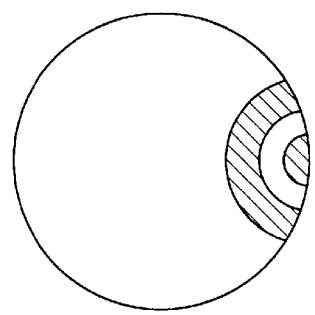
FIG. 2c illustrates a multi-zone barrier of tangential type for similar optical sculpting pattern on the anterior surface of the cornea or stromal bed.
Figure 2D:
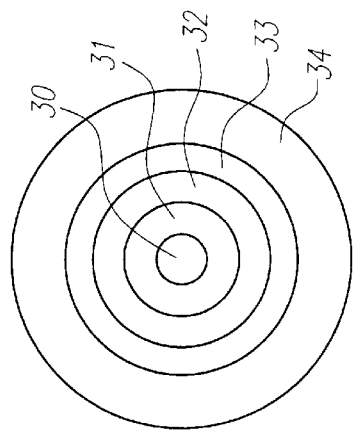
FIG. 2d represents a combination of the barriers of FIGS. 2b and 2c.
Figure 2B:
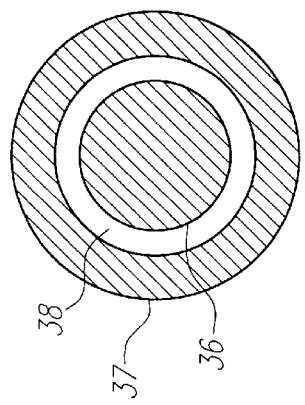
FIG. 2b illustrates a multi-zone barrier comprising concentrically located sculptured optical zones.

FIG. 2b illustrates a specific example of a one zone barrier wherein the inner and outer dark areas 36 are designed to block the sculpting energy (e.g., Excimer Laser), and with the concentric ring 38 allowing the energy to reach the cornea and thereby sculpt a ring area such as 22 of FIG. 1. It will be appreciated that other suitable mask designs can be used for sculpting the other areas; for example, a mask shown in FIG. 2a wherein only the first inner ring 31 passes sculpting energy for sculpting a ring 18 of FIG. 1. Thus FIG. 1 illustrates concentrically located sculptured optical zones on the anterior aspect of the cornea, thereby creating multiple focal lengths, and the same can be enabled by the use of barriers of the type shown in FIGS. 2a and 2b.

Turning to FIGS. 2c and 2d, the former shows a mask or barrier for providing a tangential location of a similar optical sculpting pattern on the anterior surface of the cornea. In FIG. 2D there is a combination barrier representing a combination of those similar to FIGS. 2B and 2C. Any number of rings, possibly even up to thirty-two may be used, and the pattern can be circular as illustrated in the figures, but also can have other shapes such as ovoid. The sculpting barrier or mask may be affixed to the cornea by direct apposition like a contact lens, or fixated by a suction device, to allow the laser energy to affect only the particular corneal zone selected for the corneal refractive sculpting. Thus, FIGS. 2a through 2c illustrate contact lens-like barriers or masks that block laser energy in sculpting the protected areas. These barriers may have one or multiple apertures to allow the energy to sculpt the desired refractive power, and they are constructed of materials having sections as noted which are impervious to the energy modality being used.

The technology that allows the delivery of the desired laser energy (amount and shape) can be controlled by a mask or barrier comprising a variable absorptive membrane, iris type optical diaphragm, or other suitable modalities which allow the delivery of the desired amount of energy to the cornea to create multiple zones which are concentric, asymmetric, dicentric, ovoid, and the like of varying dioptric powers and/or focal lengths. An exemplary variable absorptive membrane may comprise one or more concentric ring areas for allowing different levels of energy to pass therethrough, to thereby provide different energy levels for different concentric rings. An iris type optical diaphragm or multiple diaphragms also can be used as noted; for example, at a large opening a first level of energy is supplied to the eye to form a first outer peripheral area, then the diaphragm is stopped down to a smaller opening which allows a higher power level to be supplied for the next, inner concentric ring, and then the diaphragm is further stopped down to a smaller opening for one or more successive inner concentric rings.

The mask and/or iris diaphragm is placed (such as at 80 in FIG. 5A where a shield is shown) between the corneal epithelium, Bowman's membrane or stroma and the power source (e.g., laser energy of different wave lengths, ultrasonic energy, cryoablative energy or thermal energy). The application of the desired power then sculpts the cornea layers targeted into multiple zones of different refractive powers, thus availing the subject the capabilities of near, mid-range and distant, and/or any suitable focal length in between near and distant focus. The varying power can be administered to different concentric zones, aspheric zones, dicentric zones, circle, ovoid, or other applicable geometric shapes.

Figure 3:
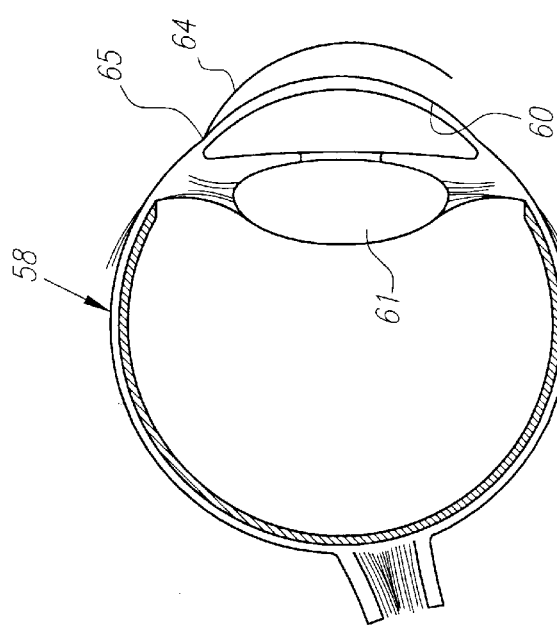
FIG. 3 is a further cross-sectional view of the eye illustrating a partial thickness cornea flap having a pedicle of the central corneal tissue attached to the remaining peripheral corneal tissue.
Figure 4A:
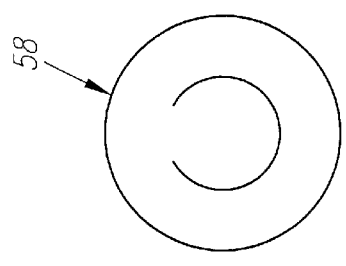
FIGS. 4a through 4c illustrate respectively a frontal view of the pedicle flap, a side view of the pedicle flap, and a side view of the pedicle flap hinged over the pedicle.
Figure 4B:
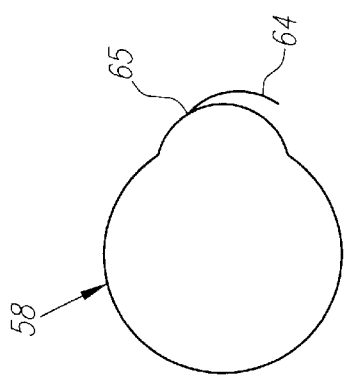
Figure 4C:
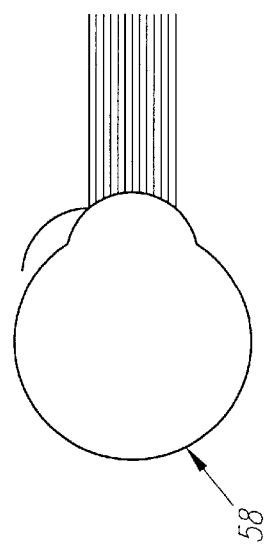

Turning now to FIGS. 3 through 5, further details of specific sculpting methods are shown and will be described below. FIG. 3 is a view similar to FIG. 1 and illustrates the cornea 60 and lens 61, but further shows a corneal flap 64 and pedicle hinge 65. FIGS. 4A through 4C further illustrate the manner in which this flap 64 is formed and hinged prior to the sculpting procedure. In one application, the corneal sculpting is performed on the stroma with a Lasik excimer procedure. In this method as illustrated in FIGS. 3–5, a corneal surgical micro keratome is used to elevate a partial thickness corneal flap 64 leaving a pedicle 65 of central corneal tissue attached to the remaining peripheral corneal tissue 60. The central circular corneal flap 64, which is still attached by the small pedicle 65, is lifted and bent back as seen in FIG. 4C using the pedicle 65 as a hinge. The sculpting shield or barrier or iris diaphragm is then positioned to allow sculpting of the corneal stroma by an excimer laser. In this method, the desired refractive sculptured surface of the cornea is accomplished by placing the appropriate shield or barrier either on the stromal surface or by placing an intervening device (i.e. iris type diaphragm, collimating mirrors, or by imputing the appropriate data into an existing energy delivery software for the excimer laser).

Figure 5B:
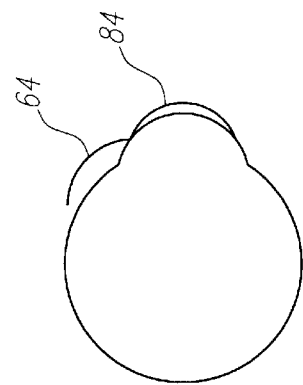
FIGS. 5a and 5b illustrate respectively a multifocal sculpturing barrier disposed between the surface of the cornea and the source of laser energy, and a barrier placed on the corneal stroma bed.
Figure 5A:
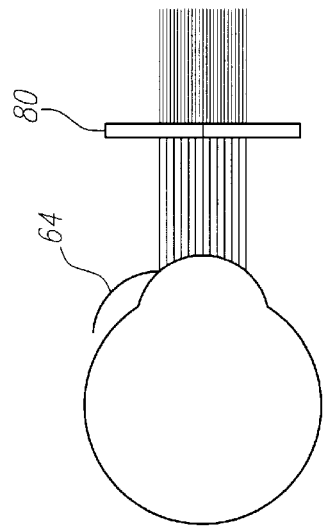

FIG. 5a illustrates a sculpting shield 80, similar to any of those of FIGS. 2A–2C, to form a multifocal sculpting barrier, and FIG. 5B shows an alternative arrangement wherein the barrier 84 is placed on the stromal surface to accomplish the multifocal sculpting.

Once the desired corneal sculpting of the stromal bed is completed to achieve the multifocal and/or astigmatic refraction has been accomplished, the pedicle flap 64 is then replaced over the corneal stromal bed. The patient is then examined at a slit lamp and a fluorescein drop is placed on the cornea to evaluate the apposition of the wound margins.

In a further application of the concepts of the present invention, corneal sculpting of the multifocal surface alone or in conjunction with an astigmatic corrective pattern can be accomplished by first removing the epithelium of the cornea (as by mechanically or by a laser), and then intervening a mask or by using an iris type diaphragm, or other techniques previously described, to control the amount of energy delivered to the different multifocal foci, then the excimer laser or other energy source is directed to the cornea surface to accomplish the desired dioptric result. At the end of the procedure, a disposable Plano contact lens can be placed on the cornea and left in place for several days and then removed. This contact lens will aid in healing. The correct positioning of the contact lens is verified after surgery by slip lamp examination. The various surgical procedures described herein can be done under topical anesthesia and as outpatient procedures.

What is claimed:

1. A method of forming a multifocal refractive surface on the cornea and in the stromal bed of an eye comprising placing a first mask between a sculpting energy source and the cornea of the eye, and applying energy through the mask toward the cornea of the eye to sculpt a first refractive surface of a first power, and disposing a second corneal mask between the source and cornea and applying energy to sculpt a second refractive surface of different power from the first.

2. A method according to claim 1 further comprising disposing a third mask, having different masking characteristics than the first and second masks, between the energy source and cornea, and directing energy therethrough to sculpt another refractive surface having a power different from at least one of the first and second refractive surfaces.

3. A method as in claim 1 wherein at least one of the masks comprises a ring concentric with the center thereof for forming a refractive surface in the shape of a ring.

4. A method as in claim 1 wherein the masks comprise an iris diaphragm.

5. A method as in claim 4 wherein the first mask comprises a first opening of the diaphragm and the second mask comprises a second, smaller opening of the diaphragm.

6. A method as in claim 1 wherein the first and second masks comprise a barrier having a plurality of concentric rings.

7. A method as in claim 6 wherein the concentric rings have different absorptive characteristics allowing different levels of laser energy penetration for each concentric ring.

8. A method as in claim 1 wherein the masks are placed for sculpting on the anterior surface of the cornea or stromal bed.

9. A method as in claim 1 wherein at least one mask is placed concentrically with respect to the eye to sculpt at least one concentric optical zone and another mask is tangentially placed for sculpting a pattern on the anterior surface of the cornea or stromal bed.

10. A method of forming a multifocal refractive surface on the cornea and in the stromal bed of an eye comprising placing a mask between a sculpting energy source and the cornea of the eye, the mask having concentric rings with different absorptive characteristics, and applying energy through the mask toward the cornea of the eye to allow different levels of penetration of energy for each concentric ring to sculpt a plurality of different refractive surfaces of different powers.

11. A method as in claim 10 wherein the mask is placed concentrically with respect to the cornea of the eye, and further comprising the step of tangentially placing a mask for sculpting a pattern on the anterior surface of the cornea or stromal bed.

12. A method of forming a multifocal refractive surface for the cornea of the eye comprising placing a first mask between a sculpting energy source and the cornea of the eye, and applying energy through the mask toward the cornea of the eye to sculpt a first refractive surface of a first power, and disposing a second corneal mask between the source and cornea and applying energy to sculpt a second refractive surface of different power from the first.

* * * * *